United States Patent
Andersson et al.

(10) Patent No.: US 11,204,346 B2
(45) Date of Patent: Dec. 21, 2021

(54) GAS SENSOR WITH FILTER

(71) Applicant: SENSIRION AG, Stäfa (CH)

(72) Inventors: Pernilla Andersson, Stäfa (CH); Roman Pavelko, Stäfa (CH); Aline Rotzetter, Stäfa (CH)

(73) Assignee: SENSIRION AG, Stafa (CH)

( * ) Notice: Subject to any disclaimer, the term of this patent is extended or adjusted under 35 U.S.C. 154(b) by 330 days.

(21) Appl. No.: 16/334,063

(22) PCT Filed: Sep. 21, 2016

(86) PCT No.: PCT/CH2016/000123
§ 371 (c)(1),
(2) Date: Mar. 18, 2019

(87) PCT Pub. No.: WO2018/053656
PCT Pub. Date: Mar. 29, 2018

(65) Prior Publication Data
US 2019/0250135 A1 Aug. 15, 2019

(51) Int. Cl.
| | |
|---|---|
| *G01N 33/00* | (2006.01) |
| *G01N 27/12* | (2006.01) |
| *B01D 53/22* | (2006.01) |
| *B01D 71/36* | (2006.01) |
| *G01N 1/40* | (2006.01) |

(52) U.S. Cl.
CPC ....... *G01N 33/0014* (2013.01); *B01D 53/228* (2013.01); *B01D 71/36* (2013.01); *G01N 1/4077* (2013.01); *G01N 27/12* (2013.01); *G01N 27/125* (2013.01); *G01N 33/0009* (2013.01); *G01N 2001/4088* (2013.01)

(58) Field of Classification Search
CPC .. G01N 33/0014; G01N 27/12; G01N 1/4077; G01N 27/125; G01N 33/0009; G01N 2001/4088; G01N 27/126; G01N 27/128; G01N 2223/6116; B01D 53/228; B01D 71/36; B81B 2201/0214; B32B 2457/14; G01J 2003/2816; G05B 2219/45031
See application file for complete search history.

(56) References Cited

U.S. PATENT DOCUMENTS

| | | |
|---|---|---|
| 5,051,114 A | 9/1991 | Nemser et al. |
| 5,703,173 A | 12/1997 | Koloski et al. |

(Continued)

FOREIGN PATENT DOCUMENTS

| | | |
|---|---|---|
| DE | 197 08 770 C1 | 8/1998 |
| DE | 10 2004 033 457 A1 | 2/2006 |

(Continued)

OTHER PUBLICATIONS

Resnick, Fluoropolymers 2, 1999, Kluwer Academic/Pluenum Publishers, p. 25 (Year: 1999).*

(Continued)

*Primary Examiner* — Eric S. McCall
*Assistant Examiner* — Timothy P Graves
(74) *Attorney, Agent, or Firm* — Ladas & Parry LLP

(57) ABSTRACT

A gas sensor comprises a support structure with a cavity (6), a sensing element (1) sensitive to a gas and arranged in the cavity (6), and a filter (3) spanning the cavity (6). The filter (3) is a size selective filter.

32 Claims, 3 Drawing Sheets

(56) References Cited

U.S. PATENT DOCUMENTS

| | | | |
|---|---|---|---|
| 5,985,673 | A | 11/1999 | Bao et al. |
| 6,012,327 | A | 1/2000 | Seth et al. |
| 6,165,336 | A * | 12/2000 | Maki ................ G01N 27/4074 204/415 |
| 6,500,547 | B1 | 12/2002 | Potyrallo |
| 6,534,319 | B1 | 3/2003 | Liu |
| 6,700,174 | B1 | 3/2004 | Miu et al. |
| 6,723,152 | B2 * | 4/2004 | Bikson ................ B01D 53/228 95/45 |
| 8,902,604 | B2 | 12/2014 | Zoellin et al. |
| 9,224,658 | B2 | 12/2015 | Sunier et al. |
| 2002/0033334 | A1 * | 3/2002 | Tschuncky ........... G01N 27/404 204/415 |
| 2005/0145493 | A1 | 7/2005 | Saffell et al. |
| 2008/0302672 | A1 | 12/2008 | Sandvik et al. |
| 2010/0212433 | A1 | 8/2010 | Hunziker |
| 2010/0230766 | A1 | 9/2010 | Elian et al. |
| 2011/0018076 | A1 | 1/2011 | Pahl et al. |
| 2012/0212925 | A1 | 8/2012 | Zoellin et al. |
| 2012/0297860 | A1 | 11/2012 | Izawa et al. |
| 2013/0094684 | A1 | 4/2013 | Ehrenpfordt et al. |
| 2013/0126992 | A1 | 5/2013 | Ehrenpfordt et al. |
| 2013/0263996 | A1 | 10/2013 | Holliday |
| 2014/0028340 | A1 | 1/2014 | Graf et al. |
| 2015/0143874 | A1 * | 5/2015 | Hunziker ........... G01N 33/0009 73/31.06 |
| 2015/0226585 | A1 * | 8/2015 | Yang .................... G01D 11/245 73/431 |
| 2015/0362451 | A1 | 12/2015 | Hunziker et al. |
| 2016/0011134 | A1 | 1/2016 | Kuemin et al. |
| 2016/0025517 | A1 | 1/2016 | Giedd et al. |
| 2016/0336141 | A1 | 8/2016 | Metkel et al. |
| 2016/0279601 | A1 | 9/2016 | Osswald |

FOREIGN PATENT DOCUMENTS

| | | |
|---|---|---|
| DE | 10 2005 043 690 A1 | 3/2007 |
| EP | 0 115 953 A2 | 8/1984 |
| EP | 0 311 439 A2 | 10/1988 |
| EP | 2 273 261 A1 | 1/2011 |
| EP | 2 373 261 | 10/2011 |
| EP | 2 778 667 | 9/2014 |
| EP | 3 196 639 A1 | 7/2017 |
| EP | 3 382 380 A1 | 10/2018 |
| JP | 2002-052338 A | 2/2002 |
| JP | 4401445 | 11/2009 |
| JP | 2010-25717 | 2/2010 |
| JP | 4542248 | 7/2010 |
| JP | 2011-212565 A | 10/2011 |
| JP | 5340910 | 8/2013 |
| JP | 2015-127642 A | 7/2015 |
| JP | 6327635 | 4/2018 |
| WO | 93/09862 | 5/1993 |
| WO | 2004/059307 | 7/2004 |
| WO | 2014/012951 | 4/2006 |
| WO | 2006/042546 | 1/2014 |

OTHER PUBLICATIONS

EP 2 373 261 _ Espacenet English Abstract.
DE 19708770 _ Espacenet English Abstract.
DE 10 2004 033 457 A1 _ Espacenet English Abstract.
DE 10 2005 043 690 A1 _ Espacenet English Abstract.
JP 2002-052338 A _ Espacenet English Abstract.
JP 2010-25717 A _ Espacenet English Abstract.
JP 2011-212565 A _ Espacenet English Abstract.
JP 2015-127642 _ Espacenet English Abstract.

Th. Becker, et al.: Ozone detection using low-power-consumption metal-oxide gas sensors: Sensors and Actuators, 74, 1999, pp. 229-232.
J.M. Bose, et al: Micromachined Structure Reliability Testing Specificity. The Motorola MGS1100 Gas Sensor Example: Microelectron. Reliab., vol. 37, No. 10/11, pp. 1791-1794, 1997.
A. Cabot, et al.: Misoporous Catalytic Filters for Semiconductor Gas Sensors: Thin Solid Films, 436, (2003), pp. 64-69.
Maximilian Fleischer, et al.: Selective gas detection with high-temperature operated metal oxides using catalytic filters: Sensors and Actuators B 69, 2000, pp. 205-210.
S. C. Gadkari, et al.: Solid State Sensors for Toxic Gases: Founder's Day Special Issue, 2005, pp. 49-60
O. Hugon, et al.: Gas separation with a zeolite filter, application to be selectivity enhancement of chemical sensors: Sensors and Actuators B 67, 2000, pp. 235-243.
Noriya Izu, et al.: Application of $V_2O_5/WO_3/TiO_2$ for Resistive-Type $SO_2$ Sensors: Sensors 2011, 11, pp. 2982-2991.
A. Katsuki, et al.: $H_2$ selective gas sensor based on $SnO_2$: Sensors and Actuators, B 52 (1998), pp. 30-37.
G. Koroteenkov: The role of morphology and crystallographic structure of metal oxides in response of conductometric-type gas sensors: Materials Science and Engineering: R 61, (2008), pp. 1-39.
G. Koroteenkov, et al.: Engineering approaches for the improvement of conductometric gas sensor parameters: Part 1. Improvement of sensor sensitivity and selectivity (short survey): Sensors and Atuators B 188 (2013) 709-728.
Konrad Maiera, et al.: Room-temperature dosimeter-type gas sensors with periodic reset: Sensors and Actuators B 244, (2017), pp. 701-708.
Rajeev S. Prabhakar, et al.: Gas and Vapor Sorption and Permeation in Poly(2,2,4-trifluoro-5-triflouromethoxy-1,3-dioxole-co-tetrafluoroethylene): Macromolecules 2004 American Chemical Society, 87, pp. 7688-7697.
SGX Sensortech (IS) Ltd Registered in England No. 08067077: SGX Metal Oxide Gas Sensors (How to Use Them and How They Perform): AN-0172, Issue 1, Jul. 14, 2014.
Nicholas F. Szabo, et al.: Strategies for total $No_X$ measurement with minimal CO interference utilitzing a microporous zeolite catalytic filter: Sensors and Actuators B 88, (2003), pp. 168-177.
Teflon Industrial: https://www.chemours.com/Teflon_Industrial/en_US/products/ product_by_name/teflo . . . Sep. 14, 2015, Availability of Licenses.
G. Tournier, et al.: Selective filter for $SnO_2$-based gas sensor: Sensors and Actuators B 106, (2005), pp. 55-562.
Montserrat Vilaseca, et al.: Gas detection with $SnO_2$ sensors modified by zeolite films: Sensors and Actuators B 124, (2007), pp. 99-110.
Dominic J. Wales, et al.: Gas sensing using porous materials for automotive applications: Chem. Soc. Rev., Jul. 7, 2015, vol. 44, No. 13, pp. 4290-4321.
Chengxiang Wang, et al.: Metal Oxide Gas Sensors: Sensitivity and influencing Factors: Sensors 2010, 10, pp. 2088-2106.
Brian G. Trewyn, et al.: Synthesis and Functionalization of a Mesoporous Silica Nanoparticle Based on the Sol-Gel Process and Applications in Controlled Release: Acc. Chem. Res. 2007, vol. 40, No. 9, pp. 846-853.
Gerhard Muller, et al.: A MEMS toolkit for metal-oxide-based gas sensing systems: Thin Solid Films 436, (2003), pp. 34-45.
Yuri Yampolskii, et al.: Materials Science of Membranes for Gas and Vapor Separation: 2006.
S. Yasunaga, et al.: Effects of Tetraethyl Orthosilicate Binder on the characteristics of an $SnO_2$, Ceramic-Type Semiconductor Gas Sensor: Sensors and Actuators, 9 (1986) 133-145.
Hong Zhang and Stephen G. Weber: Teflon AF Materials: Top Curr Chem (2012) 308: 307-338.

* cited by examiner

GAS SENSOR WITH FILTER

RELATED APPLICATION

This application is a national phase entry under 35 USC 371 of International Patent Application No.: PCT/CH2016/000123 filed on 21 Sep. 2016, the contents of which should be understood to be incorporated.

TECHNICAL FIELD

The invention relates in general to the field of gas sensors.

BACKGROUND ART

Gas sensors are known for detecting gases based on a variety of techniques. However, a sensing element of the gas sensor representing the element at which a gaseous component is converted into a representative electrical signal may adversely be affected by the impact of other gases as constituent of the medium to be measured.

DISCLOSURE OF THE INVENTION

Hence, it is a general object of the invention to provide a gas sensor avoiding such impact.

According to a first aspect of the present invention, a gas sensor is provided comprising a support structure with a cavity. A sensing element is arranged in the cavity. The sensing element is sensitive at least to the gas desired to be sensed or detected. A filter spans the cavity. The filter is a size selective filter.

The support structure of the gas sensor may be interpreted broadly in that any element that defines or co-defines the physical appearance of the gas sensor can contribute to the support structure. Specifically, the support structure as used herein may contain one or more of a die, a chip, a substrate, e.g. a glass substrate or a ceramic substrate or a semiconductor substrate, and in particular a silicon substrate, including if needed, means for electrical contacting, e.g. one or more of wire bonds, through-silicon-vias, etc. The support structure may, in addition or alternatively include a lead frame or a printed circuit board or other type of circuit board onto which the die, chip or substrate etc. may be arranged, e.g. for contributing to a ball grid array, a land grid array, etc. In an embodiment, the support structure may comprise a package, e.g. in form of an encapsulation, a mold, a silicon cap, a silicon interposer, a metal cap, a plastic cap, etc., in particular for contributing to a chip package.

One or more elements of the support structure may serve as a mechanical support of the sensing element. In one embodiment, the sensing element is arranged on or integrated in a die or a chip. The same or other elements of the support structure preferably define the cavity. The cavity is considered as a volume in direct communication with the sensing element, which volume is supposed to be filled with a gaseous medium, such as air, a gaseous analyte, also referred to as gas, is desired to be detected as to its presence and/or concentration in the medium. Hence, at least elements of the support structure define the cavity, in particular in combination with the filter.

In one embodiment, the support structure comprises a semiconductor chip supporting the sensing element, and an encapsulation at least partially encapsulating the semiconductor chip. Preferably, the encapsulation may be a mold compound molded onto parts of the semiconductor chip thereby defining a recess in the mold compound providing access to the sensing element on or in the semiconductor chip. Hence, the encapsulation may, together with the semiconductor chip and with the filter define the cavity. In this embodiment, a top surface or the encapsulation from which top surface the access opening emanates towards the sensing element may be covered by the filter such that the filter spans the access opening and defines the cavity as a volume between the filter as cover, the encapsulation as side walls, and the semiconductor chip as bottom of the cavity. The sensing element at least is exposed to the cavity, which includes the sensing element having access to the gaseous medium present in the cavity.

In a different embodiment, the support structure comprises a circuit board, such as a printed circuit board, onto which a semiconductor chip including the sensing element is arranged, and preferably electrically connected to by soldering, such as by surface mounting. A cap, preferably made from metal, preferably is attached to the printed circuit board in a sealed manner or otherwise be arranged to enclose, together with the printed circuit board, the semiconductor chip and thereby define the cavity, in which the semiconductor chip is arranged.

For the purpose of the gaseous medium to be investigated by means of the sensing element, the medium is required to enter the cavity which preferably is achieved through the filter covering the cavity. Preferably, an opening in the support structure is completely spanned by the filter in order to define the cavity, and in order to block any gas molecules to reach the cavity that has not passed the filter.

The sensing element is sensitive to one or more gas sensor that is/are desired to be detected by the present gas sensor, and preferably are desired to be detected in the gaseous medium having entered the cavity through the filter. Hence, the sensing element preferably is sensitive to the presence or concentration of one or more gases. The sensing element may in one embodiment be a catalytic gas sensing element, or pellistor, which detects the presence of combustible gases. In pellistors, a detector element provides an electrical resistance measurement dependent on the presence of a combustible gas. In particular, the resistance in the detector element varies with changes in temperature produced by the catalytic oxidation of a combustible gas if present. To facilitate the combustion of the gas, the sensors are operated at an elevated temperature, i.e., typically larger than 300° C., for example from 450° C. to 750° C. In a different embodiment, the sensing element represents an electrochemical cell.

In another embodiment, the sensing element comprises a chemiresistor, i.e., a material for which the electrical resistance changes in response to changes in their direct chemical environment. Chemiresistors are sometimes defined as relying on direct chemical interactions between the sensing material and the gas. More general definitions of chemiresistors, however, include materials for which the electrical resistance changes in response to any type of interactions (chemical, hydrogen bonds, van der Waals, etc.) in their direct environment.

In each case, the material of the sensing element may contain a metal oxide material, which may for instance include one or more of tin oxide, zinc oxide, titanium oxide, tungsten oxide, indium oxide and gallium oxide. Metal oxides may be used for the detection of analytes such as volatile organic compounds (VOCs), carbon monoxide, nitrogen dioxide, methane, ammonia, hydrogen or hydrogen sulphide. In a preferred embodiment, the sensing element comprises $SnO_2$, doped with 0.01-5.0 Wt % platinum and/or palladium.

In metal oxide gas sensors, gaseous analytes interact with the preferably bested metal oxide sensing element. As a result of the interaction, an electrical conductivity of the sensing element may change, and the change may be measured. Such gas sensors are also referred to as "high temperature chemiresistors" for the reason that a chemical property of the analyte is converted into an electrical resistance at high temperatures of the sensing element. The material of such sensing element may be required to be heated during operation. In case of the sensing element being integrated in or onto a semiconductor substrate, a heater is advantageously arranged on a membrane over an opening in the semiconductor substrate, thereby reducing the thermal loss as compared to devices where the heater is arranged over the bulk of the substrate material. Arranging the heater on a membrane has several advantages, such as reducing power consumption, and reducing the time required for switching on the device.

The filter granting or denying access to the cavity and hence to the sensing element is a size selective filter. Hence, the filter performs a separation between gas molecules allowed to pass the filter and gas molecules blocked from passing through the filter subject to the size of the gas molecules. The filter preferably is made from a material that is inert, i.e. a material that is not or not substantially reactive. Therefore, gas molecules—irrespective if passing through the filter or not—do not react with the filter material but are blocked because of their size. This has the advantage that the filter material does not degrade over time compared to a filter material chemically reacting with non-desired gas molecules.

Hence, the selection between gases to pass the filter and gases blocked by the filter is made according the size of the respective gas molecules. It is preferred that the size selective filter filters subject to the molecule size of gas encountering the size selective filter. Preferably, the size selective effect of the filter is determined by a size of pores in the filter material. In particular, the size of the pores in the filter material is dimensioned dependent on a size of a molecule of the gas to be detected and hence desired to pass the filter. In particular, the size of a majority of the pores in the filter material is dimensioned to let a/the molecule/s of the gas to be detected pass and is dimensioned to block a/the molecule/s of one or more other gases, that are to be prevented from entering the cavity. Preferably, the size of a majority of the pores in the filter material is dimensioned to exceed the size of a molecule of the gas to be detected, and is dimensioned smaller than the size of a molecule of a gas to be blocked iron passing the filter. Preferably, the material of the filter is selected and/or designed to such filtering effect.

Hence, it is preferred that the filter is permeable for the gas to be detected by the sensing element and non-permeable for one or more other gases. Such other gases may in particular include siloxane and variants thereof which are prone to react with the material of the sensing element and degrade its sensing capabilities over time. Hence, the size selective filter counteracts ingress of one or more types of atmospheric gases to the sensing element, i.e. preferably, the MOX, while allowing other types of gas molecules to diffuse there through and reach the sensing element. Thus, the filter makes it possible to counteract the ingress of inhibiting and/or poisoning species to the sensing element, and this operates by size exclusion.

In a very preferred embodiment, the size of a majority of the pores in the filter material is 1 nm or less. This dimension, in particular, is preferred in case the sensing element is configured to sense one or more of CO, Ethanol, $H_2$, $H_2S$. Here, gas molecules of the subject gases of interest are sufficiently small to pass the filter while many kinds of siloxane molecules are too big in size to pass, and hence, will be blocked by the filter.

Whenever it comes to the dimensioning or pore sizes, it is understood, that preferably all pores of the subject material fulfil the dimensional requirements. However, owed to manufacturing, not all but a lower percentage of pores may only fulfil the dimensional requirements, preferably more than 99%. In a worst case, it is preferred that a majority of the pores in the filter material fulfil the dimensional requirement in order to achieve at least a better selection than with conventional approaches.

In a preferred embodiment, an average thickness of the filter is less than 20 um, and more preferably, is between 0.5 um and 5 um. The filter may also be considered as a filter layer spanning the access opening in the support structure. The thickness of the filter layer may not necessarily impact the filtering effect thereof. However, the thicker the filter layer is, the longer it may take gas molecules to pass the filter layer and reach the sensing element. Hence, a thick filter layer may increase a response time of the subject gas sensor. Hence, it is preferred to make the filter layer rather thin, e.g. in the above ranges, in order not only to provide a size selective separation of gas molecules by the filter but also to allow a fast response time of the gas sensor. The filter may be embodied as single filter layer or as multiple filter layer stacked.

In view of the filter possibly being very thin, it may be preferred that the filter is attached to a carrier, and that a combination of the carrier and the filter spans the cavity. Preferably, the filter is attached to the carrier, or vice versa, by means of coating or solution casting. Preferably, the filter is attached laminar to the carrier or vice versa. In a preferred embodiment, the combination of the filter and the carrier span the access opening in a common plane and are attached to each other. In one embodiment, the filter and the carrier are equal in planar extension. The carrier may either carry the filter, or may at least support mechanical stability of the filter. It may also prevent the filter from becoming cracks.

In particular in order to provide mechanical stability during manufacturing and/or later on during operation, it is preferred that an average thickness of the carrier is less than 1 mm, and preferably is between 1 μm and 500 μm. Preferably, the carrier and the filter are attached to each other prior the combination being attached to the support structure.

The carrier preferably is of a size selective filtering property that at maximum provides the same filtering effect as the filter, in order not to block gas desired to be detected from entering the cavity. Hence, in a preferred embodiment, a size of a majority of pores in the carrier material exceeds a size of the majority of pores in the filter, and in particular exceeds the size of the majority of the pores in the filter material by a factor of at least 40. By such dimensioning it is granted that gas molecules to be detected pass the combination into the cavity, while gas molecules of bigger size are at least blocked by the filter even if having passed the carrier. Preferably, the size of the majority of pores in the carrier material is 20 nm or more, and in particular is between 50 nm and 200 nm. Preferably, more than 99% of the pores in the carrier are dimensioned accordingly.

In a different embodiment, the carrier is permeable to all gas molecules, such that only the filter provides for the size selective separation between gas molecules different in size.

Preferably, the combination of the filter and the carrier is attached to the support structure by means of an adhesive.

The adhesive material may for example contain polymers or filled polymers. In a preferred embodiment, the combination is attached to the support structure such that the filter faces the cavity while the carrier faces an environment of the gas sensor. Here, the filter preferably is attached to a top surface of the support structure by means of the adhesive. In such scenario, the cavity may theoretically interact with the environment through the filter, the adhesive, or the support structure. Under the assumption that the support structure is not gas permeable, and in order to avoid gas to pass through the adhesive, it is preferred that the adhesive is gas tight or is at least of the same size selective filtering property as the filter. In case the adhesive is gas tight, it is only the filter allowing gas molecules of the desired size to pass into the cavity.

In a different embodiment, the carrier faces the cavity while the filter faces the environment of the gas sensor. Again, in case the carrier is attached to a top surface of the support structure by means of the adhesive and the adhesive is configured not to let pass gas molecules that would be blocked by the filter, such gas molecules may still pass through front ends of the carrier, even in case the carrier covers the filter completely. In this embodiment, it is preferred that the front end of the carrier, or in generally any surface of the carrier that is not covered by the filter material, the adhesive of the support structure, is covered by the adhesive as gas tight or sufficiently gas blocking material.

A material of the filter preferably comprises or consist of a fluoropolymer. Preferably, the fluoropolymer is an amorphous fluoropolymer with a free fraction per volume of at least 19%, and preferably with a free fraction per volume between 20% and 40%. For example, amorphous fluoroplastics, e.g., Hyflon AD 80 or Hyflon AD 60 can be used, or amorphous fluoroplastics Teflon AF, e.g., Teflon AF 1600 or Teflon AF 2400, or a TTD homopolymer, or a Cytop homopolymer.

The free fraction per volume FFV is defined by $$FFV=(1-V_c/V)*100\%$$

wherein V denotes the total volume and $V_c$ denotes the volume occupied by the polymer in the total volume V. Hence, the FFV is a measure for the packing of the polymer, i.e. its density.

In a homopolymer embodiment of the filter material, the filter material comprises perfluorobutenylvinylether. In a different homopolymer embodiment of the filter material, the filter material comprises 2,2,4-trifluoro-5-trifluoromethyl)-1,3-dioxole.

In copolymer embodiments of the filter material, a first component of the filter material comprises 2,2,4-trifluoro-5-(trifluoromethoxy)-1,3-dioxole while the second component of the filter material comprises tetraflouroethylene. In such an embodiment, it is preferred that the first component has a mole fraction between 20% and 99%, and the second component has a mole fraction between 1% and 80%. Specifically, the 2,2,4-trifluoro-5-(trifluoromethoxy)-1,3-dioxole has a mole fraction of 80%, and the tetraflouroethylene has a mole fraction of 20%. Or, in a different embodiment, the 2,2,4-trifluoro-5-(trifluoromethoxy)-1,3-dioxole has a mole fraction of 60%, and the tetraflouroethylene has a mole fraction of 40%.

In one alternative embodiment, the filter material comprises 2,2-bistrifluoromethyl-4,5-difluoro-1,3-dioxole as a homopolymer. In a different embodiment, the filter material comprises a copolymer, wherein a first component of the filter material comprises 2,2-bistrifluoromethyl-4,5-difluoro-1,3-dioxole. Preferably a second component of the filter material comprises tetraflouroethylene. In such embodiments, the first component preferably has a mole fraction between 20% and 99%, and the second component has a mole fraction between 1% and 80%. In a specific embodiment, the 2,2-bistrifluoromethyl-4,5-difluoro-1,3-dioxole has a mole fraction of 87%, and the tetraflouroethylene has a mole fraction of 13%. In an alternate specific embodiment, the 2,2-bistrifluoromethyl-4,5-difluoro-1,3-dioxole has a mole fraction of 65%, and the tetraflouroethylene has a mole fraction of 35%.

The carrier material if any also preferably comprises or consists of a fluoropolymer. This is advantageous in that two layers of fluoropolymer, i.e. the filter and the carrier, can easily be attached to each other.

The carrier material preferably comprises Polytetrafluoroethylene PTFE or Polyethylenetetrafluoroethylene ETFE produced in the form of bulk, woven or nonwoven materials with the pore sizes specified above.

In case of the filter and the carrier both being fluoropolymers, not only the attaching effect between the filter and the layer is preferred over other material combinations; also a thermal induced extension of the materials is uniform in case of materials of the same material class.

In a preferred embodiments, electrodes are in electrical communication with the sensing element, and a heater is in thermal communication with the sensing element. This especially is preferred in case the sensing element needs to be heated prior to and/or during sensing, such as when sensing element comprises metal oxide material. A distance between the sensing element and the combination of the filter and the carrier preferably is at least 100 μm. Hence, the filter is not in direct contact with the sensing element such that a direct thermal flow from the sensing element to the filter is minimized. An indirect thermal flow via the support structure or the gaseous medium in the cavity may not allow the filter to heat up to temperatures that may exceed a critical temperature such as the glass transition temperature of the filter material during operation of the heater, i.e. during a sensing operation. Hence, any, and specifically such distance is preferred in order not to melt or otherwise affect the filter during operation of a heater of the sensor during operation. On the other hand, during e.g. reflow soldering of the gas sensor the glass transition temperatures of the filter and/or carrier material may be exceeded which however does not harm since at that point in time the gas sensor is not operated and a temporary change in the specific volume of the polymer materials may be accepted.

Thanks to the separation, distance or gap from the filter, the sensing element can be operated at elevated temperatures, e.g., higher than 350 C. or even 400 C., without damaging the filter.

In a preferred embodiment of the present invention, a top surface of the support structure is completely covered by the filter or the combination thereby spanning the cavity. This is preferred, in case of batch fabricating multiple gas sensors in combination since the filter or carrier may be applied to multiple gas sensors in combination without prior cutting the filter or carrier to the individual gas sensor size. However, for separating the gas sensors from each other by cutting, for example, a cutting tool such as a saw requires to land on the top surface of the still joined gas sensors. This top surface is represented by the filter or the carrier. Hence, in case the filter and/or carrier comprises a fluoropolymer, the landing of such cutting tool may not be easy owed to the smooth surface of fluoropolymers. In order to facilitate such cutting operation, it is preferred, that top elements are arranged on the top surface of the gas sensors, i.e. on the filter or the carrier, at positions where the cutting tool will land and/or cut. Such top elements preferably show a surface roughness exceeding the surface roughness of the top surface of the filter or carrier. The cutting tool may then land on such one or more top elements and maintain its position. After cutting, remainders of the top elements can be found at the edges of the filter or the carrier. A top element may, for example, be made from one of a polymer, a filled polymer, a mold compound, silicon, glass or metal.

In a preferred embodiment of the invention, the semiconductor chip not only comprises the sensing element arranged thereon or integrated in, but also comprises an integrated CMOS circuitry, e.g. for controlling the taking of measurements, including hearing a corresponding heater, and/or for evaluating signals provided by the electrodes.

According to another embodiment of the present invention the sensing element is embodied as a "multipixel" resistive metal oxide gas sensor, to concomitantly sense several types of gas molecules. Namely, such a sensing element preferably comprises multiple patches of sensing material, wherein each of the patches preferably comprises a metal oxide material and is arranged on or partly housed in the support structure. In addition, a set of electrodes is provided, whereby each of the patches is in electrical communication with a subset of the electrodes. One or more heaters are in thermal communication with the patches of sensing material. Finally, this gas sensor preferably comprises a common selective filter spanning a cavity common to all patches of the sensitive material.

In a preferred embodiment, the sensing element is configured to detect one of CO, Ethanol, $H_2$, $H_2S$, and hence, the gas sensor is a sensor for detecting one or more of these gases.

The present invention may for instance be embodied as an electronic device, in particular a home automation device, a consumer electronics device, a mobile phone, a tablet computer or a watch, comprising any resistive metal oxide gas sensor such as discussed above.

The present approaches prevent a degradation of a gas sensor, and specifically its sensing element, by an exposure to harmful gases. For example, siloxane, or more generally volatile Si compounds, may damage sensing elements, and in particular metal oxide sensing elements, whereby the response time of the sensing element is usually increased and the sensor signal is reduced. An exposure to such harmful gases preferably is prevented or at least mitigated by providing a filter distant from the sensing element, which filter acts as a physical separator for gas molecules of different size. It was found, that in particular a fluoropolymer filter provides for pores of the desired size letting gas molecules of smaller size to be sensed pass while, for example, blocking various siloxane gas molecules a size of which increases the size of gas molecules typically desired to be sensed. The fluorinated filter protects the sensing element against aggressive chemicals such as acids or bases, and further prevents, by design, buildup of solids and liquids on the surface of the sensing element.

BRIEF DESCRIPTION OF THE DRAWINGS

Embodiments of the invention will be better understood when consideration is given to the following detailed description thereof. This description makes reference to the annexed drawings, wherein.

MODES FOR CARRYING OUT THE INVENTION

Figure 1:
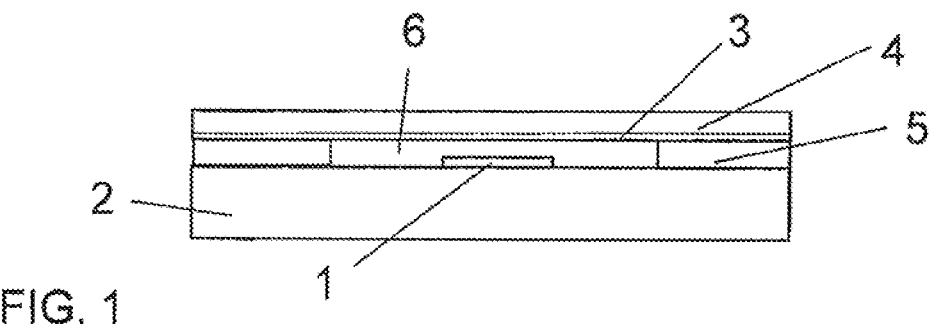
FIGS. 1 to 9 each illustrate a schematic sectional view of a gas sensor in accordance with embodiments of the present invention.

Prior to illustrating any embodiments of the gas sensor, attention is drawn to the materials used in or as filter and the carrier if any.

Preferably, the filter is made from a fluoropolymer, and preferably consists of a fluoropolymer. A fluoropolymer is a fluorocarbon-based polymer that exhibits multiple carbon-fluorine bonds. It usually has a high resistance to solvents, acids, and bases, so that it can advantageously be used for the present purpose.

For the filter, preferably an amorphous Teflon AF alike material is used according to row no. 4 of the following Table I showing preferred compositions for the filter material in each row. Row no. 4 thereby denotes an umbrella term, the other individual material compositions according to preferred embodiments in row no. 1 to row no. 3 can be subsumed under. Hence, the filter fluoropolymer may in one embodiment be a homopolymer, see row no. 3, while in the other embodiments, it is a copolymer, see row no. 1 and row no. 2.

TABLE I

| No | Name | Component 1 | Component 2 |
|----|------|-------------|-------------|
| 1 | Teflon AF 2400 | 2,2-bistrifluoromethyl-4,5-difluoro-1,3-dioxole | tetrafluoroethylene |
| 2 | Teflon AF 1600 | 2,2-bistrifluoromethyl-4,5-difluoro-1,3-dioxole | tetrafluoroethylene |
| 3 | PDD homopolymer | 2,2-bistrifluoromethyl-4,5-difluoro-1,3-dioxole | n/a |
| 4 | Teflon AF alike | 2,2-bistrifluoromethyl-4,5-difluoro-1,3-dioxole | tetrafluoroethylene |

In the following Table II properties for the individual material compositions of above row no. 1 to 4 are illustrated, wherein Comp 1, mol % denotes the mole fraction of the Component 1;

Comp 2, mol % denotes the mole fraction of the Component 2;

FFV denotes the free fraction per volume;

Tg° C. denotes the glass transition temperature of the resulting material, in ° Celsius; and Tmax denotes a maximal temperature at which polymers do not show notable degradation (i.e. thermally stable), in ° Celsius.

TABLE II

| No | Name | Comp 1, mol % | Comp 2, mol % | FFV, % | Tg, ° C. | Tmax, ° C. |
|----|------|---------------|---------------|--------|----------|------------|
| 1 | Teflon AF 2400 | 87 | 13 | 33 | 240 | 360 |
| 2 | Teflon AF 1600 | 65 | 35 | 30 | 160 | 360 |
| 3 | PDD homopolymer | 100 | 0 | >33 | 335 | 360 |
| 4 | Teflon AF alike | 100-20 | 0-80 | | 80-250 | 360 |

For the filter, alternatively, preferably a material according to one of the rows no. 5 to 9 of the following Table III is used. Row no. 8 thereby denotes an umbrella term, the other individual material compositions according to preferred embodiments in row no. 5 to row no. 7 can be subsumed under. Hence, the filter fluoropolymer may in one embodiment be a homopolymer, see row no. 7, while in the other embodiments, it is a copolymer, see row no. 5 and row no. 6. Row no. 9 indicates a further homopolymer that preferably can be used as filter material.

TABLE III

| No | Name | Component 1 | Component 2 |
|----|------|-------------|-------------|
| 5 | Hyflon AD 80 | 2,2,4-trifluoro-5-(tri-fluoromethoxy)-1,3-dioxole | tetrafluoroethylene |
| 6 | Hyflon AD 60 | 2,2,4-trifluoro-5-(tri-fluoromethoxy)-1,3-dioxole | tetrafluoroethylene |
| 7 | TTD homopolymer | 2,2,4-trifluoro-5-(tri-fluoromethoxy)-1,3-dioxole | n/a |
| 8 | Hyflon AD alike | 2,2,4-trifluoro-5-(tri-fluoromethoxy)-1,3-dioxole | tetrafluoroethylene |
| 9 | Cytop (homopolymer) | perfluoro-butenylvinylether | n/a |

In the following Table IV properties for the individual material compositions of above row no. 5 to 9 are illustrated, with the legend according to Table II.

TABLE IV

| No | Name | Comp 1, mol % | Comp 2, mol % | FFV, % | Tg, ° C. | Tmax |
|----|------|---------------|---------------|--------|----------|------|
| 5 | Hyflon AD 80 | 80 | 20 | 23 | 135 | ca. 400 C. |
| 6 | Hyflon AD 60 | 60 | 40 | 23 | 129 | ca. 400 C. |
| 7 | TTD homopolymer | 100 | 0 | | 170 | ca. 400 C. |
| 8 | Hyflon AD alike | 100-20 | 0-80 | | 170 | ca. 400 C. |
| 9 | Cytop (homopolymer) | 100 | 0 | 21 | 108 | 400 |

The carrier, if any, preferably is made from a fluoropolymer, and preferably consists of a fluoropolymer, e.g. Polytetrafluoroethylene (PTFE) or Polyethylenetetrafluoroethylene (ETFE) produced in the form of bulk, woven or nonwoven materials with the pore sizes specified above.

The sensing element preferably is represented by a patch of sensing material. In embodiments, the present sensing element can be operated as a chemiresistor, wherein a metal oxide material, the sensing element is made of, changes its electrical resistance in response to gas molecules having passed the filter, leading to chemical interactions between the material of the sensing element and the gas/analytes. In other embodiments, one may rely on a calorimetric determination of the gas/analyte. In still other embodiments, the patch of sensing material can be used for two purposes, namely: (i) as a chemiresistor that changes its electrical conductivity in the presence of the analyte; and (ii) as a catalyst in a calorimetric determination of the analyte.

In one embodiment, the latter comprises a metal oxide material, or MOX. Beyond the examples cited above, preferred MOX materials comprise $SnO_2$ and/or $WO_3$, and preferably comprises dopants too, the latter comprising one or more of Pd, Pt, Rh, Ir, Re, V, Ni, Au, and Co. The patch may be arranged on the support structure. It may for instance extend on an exposed surface of the support structure, such as a semiconductor substrate, e.g., overlaid flat on an upper surface thereof, or extend on substructures thereof, such as electrodes. Electrodes may be arranged in the gas sensor, so as to be in electrical communication with the patch of sensing material. They may be formed out of a platinum or gold layer, which metals are well suited for forming stable electrodes. Electrodes may for instance be in an interdigitated configuration. Thus, the patch in one embodiment may have a shape (e.g., convex) that spans a region that covers or includes interdigitated fingers of the electrodes.

In one embodiment, a heater is in thermal communication with the patch, to operate the sensing material at a required temperature. The header may be a resistive heating element. For example, one may use a heater of tungsten, i.e., a heater comprising at least 50%, in particular at least 90%, of tungsten, to best withstand high temperatures. Several heaters may be provided, to heat a plate (e.g., a membrane, or a bridge), on which the patch is arranged. In variants, the heater may be embodied as a hotplate, which is resistivity heated, without additional resistive elements being needed. The heater can be used to heat the patch and, if necessary, to furthermore control the temperature of. The semiconductor chip of the gas sensor preferably includes circuitry, integrated therewith, to heat the heater and perform resistive measurements, i.e., to measure an electrical conductivity and/or resistivity of the patch.

In the Figures, like elements are referred to by the same reference signs.

FIG. 1 shows a schematic sectional view of a gas sensor in accordance with an embodiment of the present invention. The gas sensor induces a sensing element 1, which is arranged on or integrated in a support structure. In this embodiment, the support structure includes a semiconductor chip 2, e.g. a silicon substrate, and an adhesive 5 which in the present embodiment is of sufficient thickness in order to form a cavity 6 in combination with a filter 3 and a carrier 4 for the filter 4.

The gas to be sensed can enter the cavity 6 and thereby reach the sensing element 1 through the carrier 4 and the filter 3. The combination of the filter 3 and the carrier 4 is attached to the semiconductor substrate 2 by means of the adhesive 5 with the filter 3 facing the cavity 6, and the carrier 4 facing the environment of the gas sensor.

Figure 2:
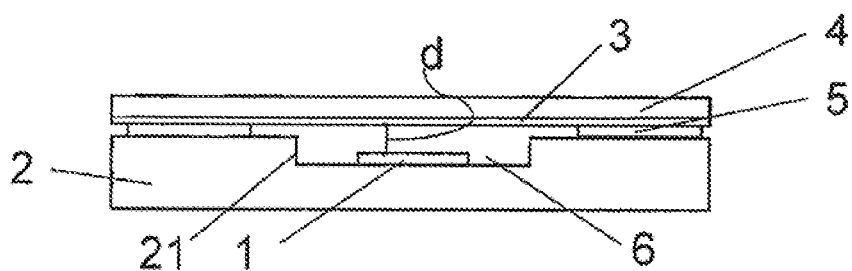

FIG. 2 shows another embodiment of a gas sensor in accordance with the present invention. In this embodiment, the semiconductor substrate 2, which also can be any other support, has a recess 21 which recess contributes to the cavity 6, and in which recess 21 the sensing element 1 is located. In this embodiment, it is not only the thickness of the adhesive 5 that provides for a sufficient distance d between the sensing element 1 and the filter 3 or carrier 4 respectively. The recessed portion of the semiconductor substrate 2 contributes to this distance d.

Figure 3:
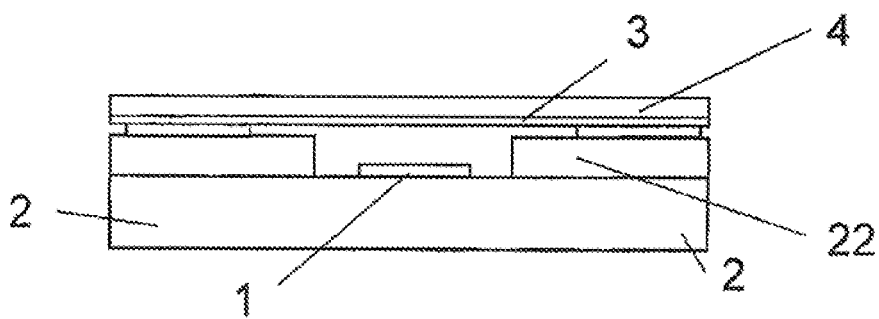

FIG. 3 illustrates another embodiment of a gas sensor in accordance with the present invention. In this embodiment, the support structure of the gas sensor contains a semiconductor substrate 2 and a spacer 22 on top of a semiconductor substrate 2, for example. The spacer 22 can be of a different material than the semiconductor substrate 2.

Figure 4:
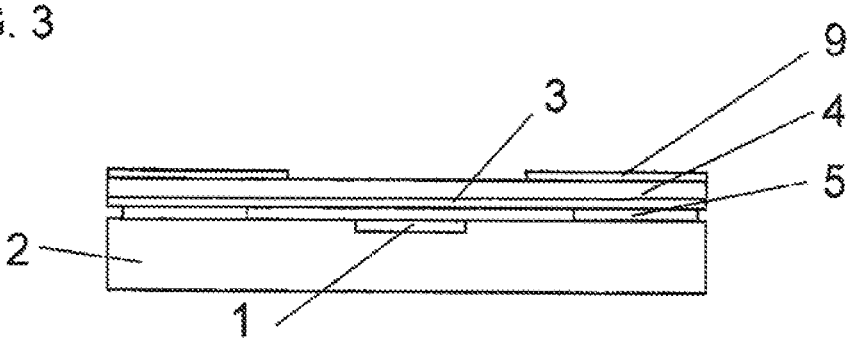

FIG. 4 shows another embodiment of a gas sensor device in accordance with the present invention. Basically, this embodiment is similar to the embodiment of FIG. 1 except for top elements 9 added on to edges of the carrier 4.

Figure 5:
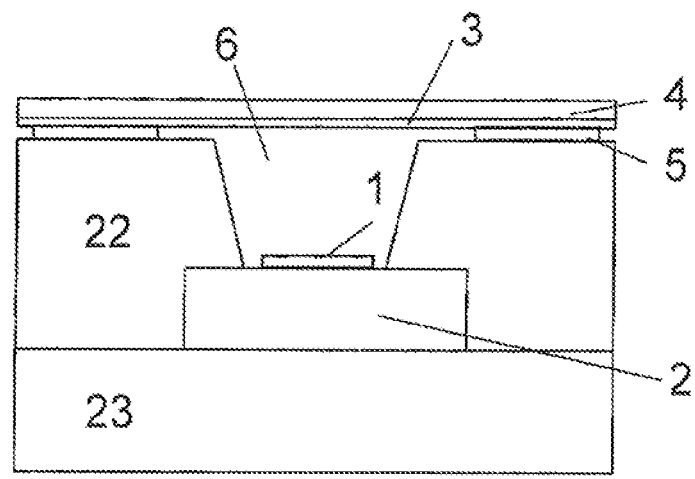

FIG. 5 illustrates another embodiment of a gas sensor in accordance with the present invention. In this embodiment, the gas sensor again comprises a semiconductor chip 2 with the sensing element 1. The semiconductor chip 2 is partly covered by an encapsulation 22 in form of a mold and a lead frame 23 serves for outside contacting. The support structure for the sensing element 1 hence includes the semiconductor chip 2, the encapsulation 22, the adhesive 5 and the lead frame 23. A cavity 6 is formed by the support structure which cavity 6 is closed by a combination of a filter 3 and a carrier 4 for the filter 3. The combination of filter 3 and carrier 4 extends over the entire top surface of the support structure 2 to which the combination, of filter 3 and carrier 4 is attached by means of the adhesive 5.

Figure 6:
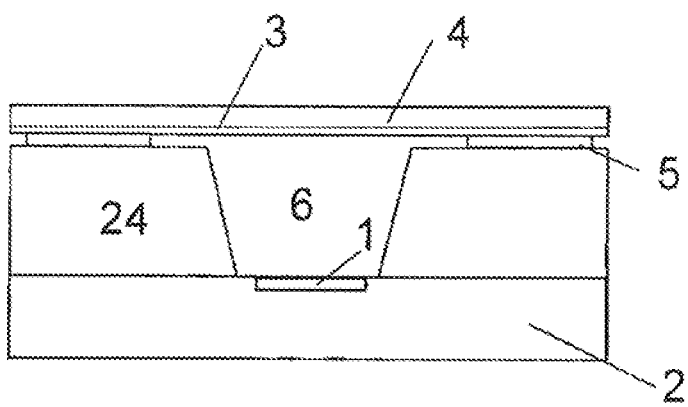

FIG. 6 illustrates another embodiment of a gas sensor in accordance with the present invention. In this embodiment, the gas sensor comprises a semiconductor chip 2 with the sensing element 1. The semiconductor chip 2 is partly covered by a silicon cap 24. A cavity 6 is formed by the semiconductor substrate 2, the silicon cap 21 and the adhesive 5, thus contributing to the support structure.

Figure 7:
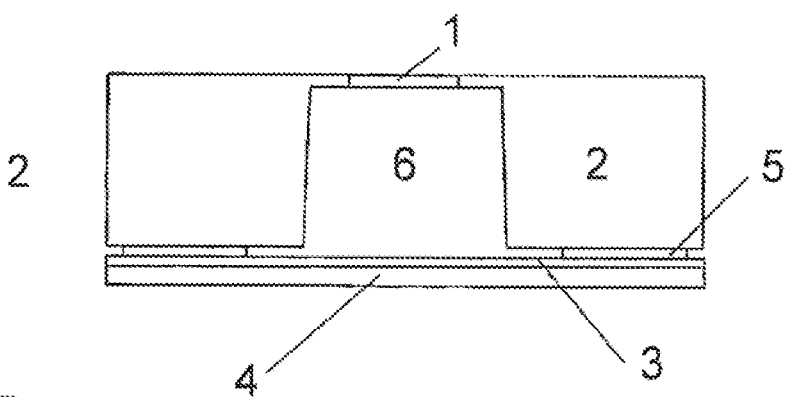

FIG. 7 illustrates another embodiment of the gas sensor in accordance with the present invention. Again, a sensing element 1 is arranged on/in a suspended membrane portion of a semiconductor substrate 2 which suspended members portion, for example, is prepared by etching substrate material from a backside of the semiconductor chip 2. This results in a cavity 6. For this reason, the combination of the filter 3 and carrier 4 is attached to a backside of the semiconductor chip 2, again by means of an adhesive 5.

Figure 8:
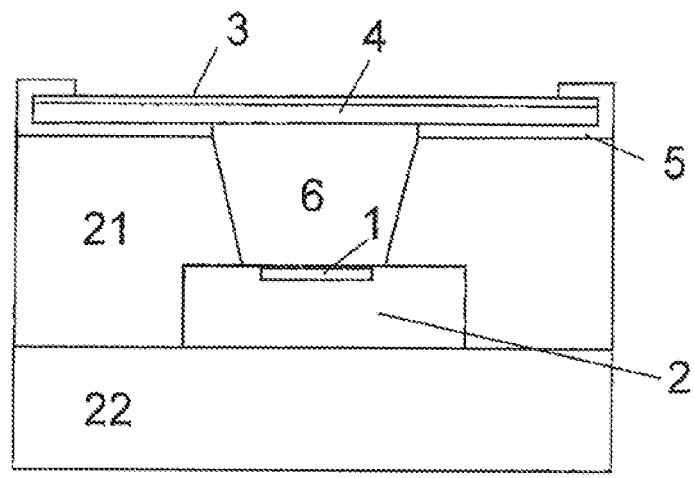

FIG. 8 illustrates another embodiment of the gas sensor in accordance with the present invention. This embodiment resembles the embodiment of FIG. 5. In contrast to the embodiment of FIG. 5, the combination of the filter 3 and the carrier 4 is attached vice versa to the top surface of the support structure by means of the adhesive 5. Hence, the carrier 4 faces the cavity 6 while the filter 3 faces an environment, of the gas sensor. Therefore, it is desired to seal a direct path from the outside of the gas sensor through the carrier 4 into the cavity 6. Such path is sealed by covering any surface of the carrier 4 that is neither covered by the filter 3 nor by the adhesive 5. For this purpose, the adhesive 5 also covers the front end of the carrier 4, and, in one embodiment is even lifted on top of the carrier 4, in order to at the same time act as top element for one of the purposes previously listed for top elements.

Figure 9:
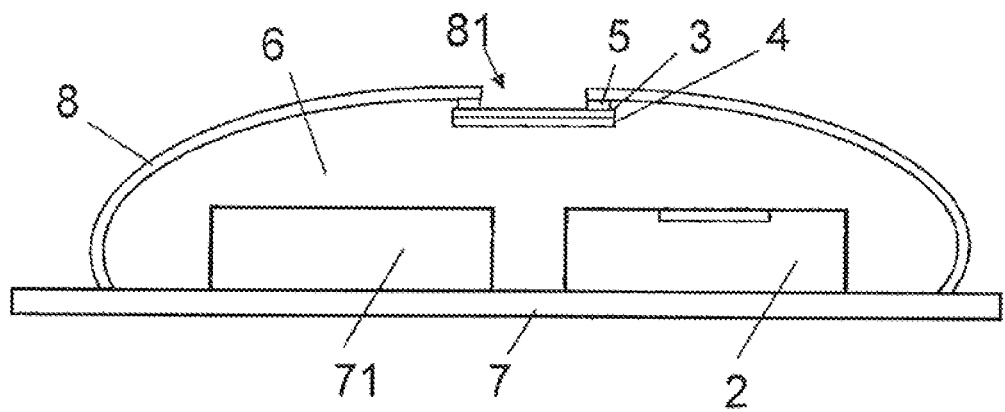

FIG. 9 illustrates another embodiment of the gas sensor in accordance with the present invention. In this embodiment, a semiconductor chip 2 including the sensing element 1 is arranged, and preferably electrically connected to a circuit board 7 such as a printed circuit board. In addition, one or more other chips such as an integrated circuit 71 may be arranged on the circuit board 7, too. A cap 8, e.g. made from metal, may, in combination with the circuit board 7 build a housing for the semiconductor chip 2, enclosing a cavity 6. The cap 8 has an opening 81, which is spanned by a combination of a filter 3 and a carrier 4. The combination is attached to the cap 6 by means of an adhesive 5, from the inside of the cap 8.

Figure 10:
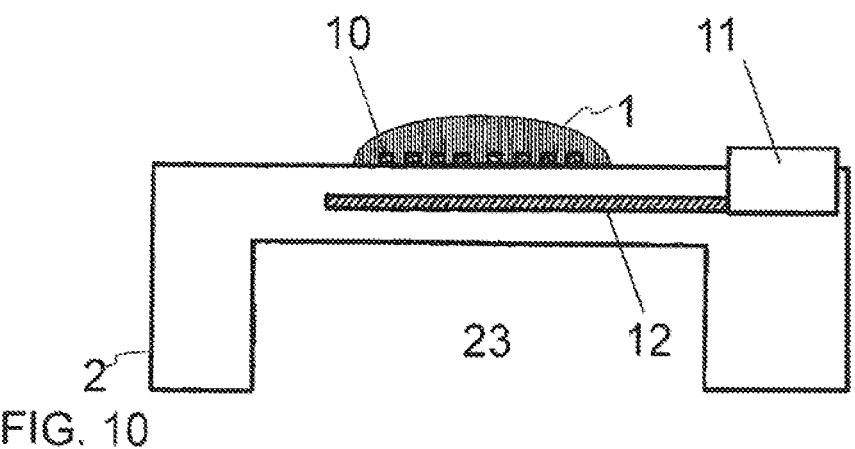
FIG. 10 illustrates a schematic sectional view of a gas sensor structure contributing to a gas sensor according to an embodiment of the present invention.

FIG. 10 illustrates a gas sensor structure contributing to a gas sensor of an embodiment of the present invention. The present structure is to be finalized by attaching a filter or a combination of a filter and a carrier to the present structure. The present gas sensor structure comprises a sensing element 1 arranged on a semiconductor chip 2 that is etched from its backside thereby defining a recess 23. The sensing element 2 covers electrodes 10 for supplying an electrical signal to an evaluation and control unit 11 to be evaluated there. The evaluation and control unit 11 preferably is integrated into the semiconductor chip 2. The evaluation and control unit 11 preferably also controls a heater 12 integrated in the semiconductor substrate 2, e.g. in the membrane remaining force the etching of the recess 23.

While there are shown and described presently preferred embodiments of the invention, it is to be distinctly understood that the invention is not limited thereto but may be otherwise variously embodied and practiced within the scope of the following claims.

The invention claimed is:
1. A gas sensor, comprising
a support structure comprising a cavity,
a sensing element sensitive to a gas and arranged in the cavity,
a filter, and
a carrier,
wherein the filter or the carrier and the filter in combination span the cavity,
wherein the filter is a size selective filter,
wherein the size selective filter filters gas molecules subject to their size, and
wherein a size of a majority of pores in the carrier material exceeds a size of a majority of pores in the filter material,
wherein a combination comprises the filter and the carrier thereby spanning the cavity,
wherein one or more top elements are arranged on a top surface and at edges of the combination, and
wherein the one or more top elements show a surface roughness exceeding a surface roughness of the top surface of the combination.

2. The gas sensor of claim 1, wherein the size selective filter is permeable for the gas to be detected by the sensing element and non-permeable for one or more other gases,
wherein the size selective effect of the filter is determined by a size of pores in the filter material,
in particular wherein the size of the pores in the filter material is dimensioned dependent on a size of a molecule of the gas to be detected,
in particular wherein the size of a majority of the pores in the filter material is dimensioned to let molecules of the gas to be detected pass and to block molecules of one or more other gases,
in particular wherein the size of a majority of the pores in the filter material is dimensioned to exceed the size of a molecule of the gas to be detected, and is dimensioned smaller than the size of a molecule of the one or more other gases to be blocked,
in particular wherein the size of a majority of the pores in the filter material is 1 nm or less.

3. The gas sensor of claim 1,
wherein the filter material comprises a fluoropolymer.

4. The gas sensor of claim 3,
wherein the filter material comprises an amorphous fluoropolymer with a free fraction per volume of at least 19%.

5. The gas sensor of claim 3
wherein the filter material comprises a homopolymer.

6. The gas sensor of claim 3,
wherein the filter material comprises 2,2,4-trifluoro-5-(trifluoromethoxy)-1,3-dioxole.

7. The gas sensor of claim 3,
wherein the filter material comprises a copolymer,
in particular wherein a second component of the filter material comprises tetraflouroethylene.

8. The gas sensor of claim 7,
wherein a first component has a mole fraction between 20% and 99%, and
wherein the second component has a mole fraction between 1% and 80%.

9. The gas sensor of claim 7,
wherein a first component of the filter material comprises 2,2,4-trifluoro-5-(trifluoromethoxy)-1,3-dioxole,
wherein the 2,2,4-trifluoro-5-(trifluoromethoxy)-1,3-dioxole has a mole fraction of 80%, and
wherein the tetraflouroethylene has a mole fraction of 20%.

10. The gas sensor of claim 7,
wherein a first component of the filter material comprises 2,2,4-trifluoro-5-(trifluoromethoxy)-1,3-dioxole,
wherein the 2,2,4-trifluoro-5-(trifluoromethoxy)-1,3-dioxole has a mole fraction of 60%, and
wherein the tetraflouroethylene has a mole fraction of 40%.

11. The gas sensor of claim 3,
wherein the filter material comprises 2,2-bistrifluoromethyl-4,5-difluoro-1,3-dioxole.

12. The gas sensor of claim 3,
wherein the filter material comprises a copolymer.

13. The gas sensor of claim 12,
wherein a first component of the filter material has a mole fraction between 20% and 99%, and
wherein a second component of the filter material has a mole fraction between 1% and 80%.

14. The gas sensor of claim 13,
wherein the first component of the filter material comprises 22-bistrifluoromethyl-4,5-difluoro-1,3-dioxole,
wherein the 22-bistrifluoromethyl-4,5-difluoro-1,3-dioxole has a mole fraction of 87%,
wherein the second component of the filter material comprises tetraflouroethylene, and
wherein the tetraflouroethylene has a mole fraction of 13%.

15. The gas sensor of claim 13,
wherein the first component of the filter material comprises 22-bistrifluoromethyl-4,5-difluoro-1,3-dioxole,
wherein the 22-bistrifluoromethyl-4,5-difluoro-1,3-dioxole has a mole fraction of 65%,
wherein the second component of the filter material comprises tetraflouroethylene, and
wherein the tetraflouroethylene has a mole fraction of 35%.

16. The gas sensor of claim 1,
wherein an average thickness of the filter is less than 20 µm.

17. The gas sensor of claim 1, comprising
electrodes in electrical communication with the sensing element,
a heater in thermal communication with the sensing element, and
wherein the sensing element comprises metal oxide material,
wherein the sensing element is configured to detect one of CO, Ethanol, $H_2$, $H_2S$.

18. The gas sensor of claim 1,
wherein the support structure comprises
a circuit board
a semiconductor chip arranged on the circuit board and supporting the sensing element,
a cap for housing the semiconductor chip,
wherein the cap contributes to forming the cavity and comprises an opening wherein the opening is spanned by the size selective filter.

19. An electronic device, which comprises one of a home automation device, a consumer electronics device, a mobile phone, a tablet computer and a watch, comprising the gas sensor according to claim 1.

20. A gas sensor, comprising
a support structure comprising a cavity,
a sensing element sensitive to a gas and arranged in the cavity,
a filter, and
a carrier,
wherein the filter or the carrier and the filter in combination span the cavity,
wherein an average thickness of the carrier is less than 1 mm,
wherein a combination comprises the filter and the carrier thereby spanning the cavity,
wherein one or more top elements are arranged on a top surface and at edges of the combination, and
wherein the one or more top elements show a surface roughness exceeding a surface roughness of the top surface of the combination.

21. The gas sensor of claim 20,
wherein the carrier is one of:
gas permeable;
of size selective filtering property.

22. The gas sensor of claim 20,
wherein the size of the majority of pores in the carrier material exceeds the size of the majority of pores in the filter material by a factor of at least 20.

23. The gas sensor of claim 20,
wherein the size of the majority of pores in the carrier material is 40 nm or more.

24. The gas sensor of claim 23,
wherein the size of the majority of pores in the carrier material is between 50 nm and 200 nm.

25. The gas sensor of claim 20,
wherein the carrier material comprises a fluoropolymer.

26. The gas sensor of claim 25,
wherein the carrier material comprises or consists of one of Polytetrafluoroethylene PTFE or Polyethylenetetrafluoroethylene ETFE.

27. The gas sensor of claim 20,
wherein an average thickness of the carrier is between 1 µm and 500 µm.

28. The gas sensor of claim 20,
wherein the combination of the filter and the carrier is attached to the support structure by means of an adhesive,
in particular wherein the adhesive is one of:
gas tight;
at least of the same size selective filtering property as the filter.

29. The gas sensor of claim 20,
wherein the filter faces the cavity and the carrier faces an environment of the gas sensor,
in particular wherein the filter is attached to a top surface of the support structure by means of an adhesive.

30. The gas sensor of claim 20,
wherein the carrier faces the cavity and the filter faces an environment of the gas sensor,
in particular wherein the filter is attached to a top surface of the support structure by means of an adhesive.

31. The gas sensor of claim 20,
wherein a distance between the sensing element and the combination of the filter and the carrier is at least 100 µm.

32. A gas sensor, comprising
a support structure comprising a cavity,
a sensing element sensitive to a gas and arranged in the cavity,
a filter, and
a carrier,
wherein the support structure comprises
a semiconductor chip supporting the sensing element, and an encapsulation at least partially encapsulating the semiconductor chip,
wherein a top surface of the encapsulation is completely covered by a combination,
wherein the combination comprises the filter and the carrier thereby spanning the cavity,
wherein one or more top elements are arranged on a top surface and at edges of the combination, and
wherein the one or more top elements show a surface roughness exceeding a surface roughness of the top surface of the combination.

\* \* \* \* \*